(12) United States Patent
Izatt et al.

(10) Patent No.: US 10,238,279 B2
(45) Date of Patent: Mar. 26, 2019

(54) STEREOSCOPIC DISPLAY SYSTEMS AND METHODS FOR DISPLAYING SURGICAL DATA AND INFORMATION IN A SURGICAL MICROSCOPE

(71) Applicant: Duke University, Durham, NC (US)

(72) Inventors: Joseph A. Izatt, Durham, NC (US); Liangbo Shen, Durham, NC (US); Oscar M. Carrasco-Zevallos, Durham, NC (US); Cynthia Toth, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/547,537

(22) PCT Filed: Feb. 5, 2016

(86) PCT No.: PCT/US2016/016830
§ 371 (c)(1),
(2) Date: Jul. 31, 2017

(87) PCT Pub. No.: WO2016/127088
PCT Pub. Date: Aug. 11, 2016

(65) Prior Publication Data
US 2018/0008140 A1 Jan. 11, 2018

Related U.S. Application Data

(60) Provisional application No. 62/112,698, filed on Feb. 6, 2015.

(51) Int. Cl.
*A61B 3/00* (2006.01)
*G02B 21/00* (2006.01)
(Continued)

(52) U.S. Cl.
CPC ............ *A61B 3/0041* (2013.01); *A61B 3/102* (2013.01); *A61B 3/132* (2013.01);
(Continued)

(58) Field of Classification Search
CPC ........... A61B 3/14; A61B 3/0025; A61B 3/12; A61B 3/102; A61B 3/0058
(Continued)

(56) References Cited

U.S. PATENT DOCUMENTS 5,040,229 A 8/1991 Lee et al.
5,483,364 A * 1/1996 Ishimoto .............. G03H 1/0808
359/15
(Continued)

FOREIGN PATENT DOCUMENTS

EP 1647370 A1 4/2006
KR 1020130000023 1/2013
(Continued)

OTHER PUBLICATIONS

Notice of Allowance received in U.S. Appl. No. 14/337,215 dated Dec. 23, 2015.
(Continued)

*Primary Examiner* — Mohammed A Hasan
(74) *Attorney, Agent, or Firm* — Olive Law Group, PLLC

(57) ABSTRACT

Stereoscopic display systems and methods for displaying surgical data and information in a surgical microscope are disclosed herein. According to an aspect, a system includes first and second eyepieces. The system includes a display having first and second display portions, configured to display first images in the first display portion, and configured to display second images in the second display portion. The first image and the second image are projected along a first pathway and a second pathway. The system includes a first optical element positioned to relay the first images into
(Continued)

the first eyepiece. The system includes a second optical element positioned to relay the second images into the second eyepiece.

17 Claims, 11 Drawing Sheets

(51) Int. Cl.
| | |
|---|---|
| *G02B 21/22* | (2006.01) |
| *A61B 3/10* | (2006.01) |
| *A61B 3/13* | (2006.01) |
| *G02B 27/01* | (2006.01) |
| *H04N 13/344* | (2018.01) |
| *H04N 13/293* | (2018.01) |
| *H04N 13/286* | (2018.01) |

(52) U.S. Cl.
CPC ......... *G02B 21/0012* (2013.01); *G02B 21/22* (2013.01); *G02B 27/0172* (2013.01); *H04N 13/293* (2018.05); *H04N 13/344* (2018.05); *G02B 2027/0134* (2013.01); *H04N 13/286* (2018.05)

(58) Field of Classification Search
USPC ......................................................... 351/206
See application file for complete search history.

(56) References Cited

U.S. PATENT DOCUMENTS

| | | | |
|---|---|---|---|
| 5,493,109 | A | 2/1996 | Wei et al. |
| 5,715,081 | A | 2/1998 | Chastang et al. |
| 5,963,301 | A | 10/1999 | Volk |
| 6,671,581 | B2 | 12/2003 | Niemeyer et al. |
| 7,791,794 | B2 | 9/2010 | Reimer et al. |
| 7,839,494 | B2 | 11/2010 | Reimer et al. |
| 7,907,166 | B2 | 3/2011 | Lamprecht et al. |
| 9,207,638 | B2 | 12/2015 | Dubois et al. |
| 2001/0031078 | A1 | 10/2001 | Doane |
| 2002/0099290 | A1 | 7/2002 | Haddad |
| 2005/0270486 | A1 | 12/2005 | Teiwes et al. |
| 2006/0050991 | A1 | 3/2006 | Jerebko et al. |
| 2007/0086647 | A1 | 4/2007 | Grady |
| 2007/0299309 | A1 | 12/2007 | Seibel et al. |
| 2008/0002183 | A1 | 1/2008 | Yatagai et al. |
| 2008/0019587 | A1 | 1/2008 | Wilensky et al. |
| 2008/0030497 | A1 | 2/2008 | Hu et al. |
| 2008/0058704 | A1 | 3/2008 | Hee et al. |
| 2009/0018393 | A1 | 1/2009 | Dick et al. |
| 2009/0060332 | A1 | 3/2009 | Knapp |
| 2009/0131921 | A1 | 5/2009 | Kurtz et al. |
| 2009/0192523 | A1 | 7/2009 | Larkin et al. |
| 2009/0225407 | A1 | 9/2009 | Nakayama et al. |
| 2009/0244485 | A1 | 10/2009 | Walsh et al. |
| 2009/0257065 | A1 | 10/2009 | Hauger et al. |
| 2009/0287223 | A1 | 11/2009 | Pua et al. |
| 2010/0202677 | A1 | 8/2010 | Imamura et al. |
| 2010/0228123 | A1 | 9/2010 | Brennan et al. |
| 2010/0331858 | A1 | 12/2010 | Simaan et al. |
| 2011/0032533 | A1 | 2/2011 | Izatt et al. |
| 2011/0043757 | A1 | 2/2011 | Everett et al. |
| 2011/0122487 | A1 | 5/2011 | Perelman et al. |
| 2012/0092615 | A1 | 4/2012 | Izatt et al. |
| 2012/0184846 | A1 | 7/2012 | Izatt et al. |
| 2012/0307205 | A1 | 12/2012 | Zhou et al. |
| 2013/0010259 | A1 | 1/2013 | Carnevale |
| 2013/0016319 | A1 | 1/2013 | Vohnsen et al. |
| 2013/0135584 | A1 | 5/2013 | Alasaarela et al. |
| 2013/0188140 | A1 | 7/2013 | Bagherinia et al. |
| 2013/0245375 | A1 | 9/2013 | DiMaio et al. |
| 2013/0293838 | A1 | 11/2013 | Makihira et al. |
| 2014/0009741 | A1 | 1/2014 | Levien et al. |
| 2014/0139916 | A1* | 5/2014 | Doi .................... G02B 21/0012 359/477 |
| 2014/0142591 | A1 | 5/2014 | Alvarez et al. |
| 2014/0247425 | A1 | 9/2014 | Hammer et al. |
| 2014/0275760 | A1 | 9/2014 | Lee et al. |
| 2014/0307315 | A1* | 10/2014 | Bohn .................. G02B 27/0176 359/480 |
| 2014/0368907 | A1* | 12/2014 | Minami ............... G02B 5/0215 359/463 |
| 2015/0173846 | A1* | 6/2015 | Schneider .......... A61B 1/00009 600/424 |

FOREIGN PATENT DOCUMENTS

| | | |
|---|---|---|
| WO | 2005106786 A1 | 11/2005 |
| WO | 2012100030 A2 | 7/2012 |
| WO | 2012109301 A2 | 8/2012 |
| WO | 2013008033 A1 | 1/2013 |
| WO | 2013180773 A1 | 12/2013 |
| WO | 2014068058 A1 | 5/2014 |

OTHER PUBLICATIONS

Notice of Allowance received in U.S. Appl. No. 15/049,103 dated Oct. 10, 2016.

Office Action received in U.S. Appl. No. 14/337,215 dated May 12, 2015.

Office Action received in U.S. Appl. No. 14/337,215 dated Nov. 5, 2014.

Office Action received in U.S. Appl. No. 15/049,103 dated Jul. 5, 2016.

Otsu, A Threshold Selection Method from Gray-Level Histograms, IEEE Transactions on Systems, Man, and Cybernetics, vol. SMC-9, No. 1, Jan. 1979, U.S.

PCT International Search Report for PCT International Application No. PCT/US15/13870.

PCT International Written Opinion for PCT International Application No. PCT/US15/13870.

PCT Preliminary Report on Patentability and Written Opinion dated May 8, 2014 for related PCT International Application No. PCT/US2014/013243.

PCT Search Report and Written Opinion dated Jul. 13, 2012 for related application PCT/US2012/021839; iFD Jan. 19, 2012.

Perstein, M., Algorithms, Control Data Corp., Palo Alto, California.

Pircher, Michael et al., Simultaneous SLO/OCT Imaging of the Human Retina with Axial Eye Motion Correction, Optics Express, vol. 15, No. 25, Dec. 4, 2007.

Related application PCT/US2012/021839 filed Jan. 19, 2012 entitled System Enhancements for Ophthalmic Surgical Microscope Mounted Optical Coherence Tomography, not yet published.

Schulze, Jürgen P. et al.; "Visualization of Three-Dimensional Ultra-High Resolution OCT in Virtual Reality" Ophthalmology Department, Lariboisière Hospital, APHP, Paris, France.

SDI/BIOM: Still the Standard in Wide-Angle Viewing for All Microscope Models!, Insight Instruments, Inc., Stuart, Florida.

Shen, Liangbo et al.; "Novel Microscope-Integrated Stereoscopic Heads-up Display for Intrasurgical OCT in Ophthalmic Surgery", The Association for Research in Vision and Ophthalmology; Jun. 2015, vol. 56, 3514.

Shi et al., Normalized Cuts and Image Segmentation, IEEE Transactions on Pattern Analysis and Machine Intelligence, vol. 22, No. 8, Aug. 2000, U.S.

Shi, Minyan et al.; "A Stereo-Fluoroscopic Image-Guided Robotic Biopsy Scheme" IEEE Transactions on Control Systems Technology, vol. 10, No. 3, May 2002, pp. 309-317.

Stephanie J. Chiu, Cynthia A. Toth, Catherine Bowes Rickman, Joseph A. Izatt, and Sina Farsiu, "Automatic Segmentation of Cloaed-contour Features in Ophthalmic Images Using Graph Theory and Dynamic Programming", Published Apr. 26, 2012, Optical Society of America.

Takeda et al., Kernel Regression for Image Processing and Reconstruction, IEEE Transactions on Image Processing, vol. 16, No. 2, Feb. 2007, U.S.

The Age-Related Eye Disease Study Research Group, The Age-Related Eye Disease Study System for Classifying Age-Related

(56) References Cited

OTHER PUBLICATIONS

Macular Degeneration From Stereoscopic Color Fundus Photographs: The Age-Related Eye Disease Study Report No. 6, Elsevier Service Inc., vol. 132, No. 5, 2001, U.S.
Tolliver et al., Unassisted Segmentation of Multiple Retinal Layers via Spectral Rounding, Presented in ARVO 2008 Annual Meeting, Fort Lauderdale, Florida, U.S., Apr. 2008.
U.S. Final Office Action for U.S. Appl. No. 14/337,215, dated May 12, 2015.
U.S. Non-Final Office Action for U.S. Appl. No. 13/010,448, dated Jan. 2, 2014.
U.S. Non-Final Office Action for U.S. Appl. No. 14/337,215, dated Nov. 5, 2014.
U.S. Non-Final Office Action for U.S. Appl. No. 15/049,103, dated Jul. 5, 2016.
U.S. Notice of Allowance for U.S. Appl. No. 1301448, dated May 13, 2013.
U.S. Notice of Allowance for U.S. Appl. No. 14/337,215, dated Jan. 11, 2016.
U.S. Notice of Allowance for U.S. Appl. No. 15/049,103, dated Oct. 24, 2016.
U.S. Office Action Response to Non-Final Office Action for U.S. Appl. No. 14/337,215, dated Apr. 6, 2015.
U.S. Office Action Response to Non-Final Office Action for U.S. Appl. No. 15/049,103, dated Oct. 6, 2016.
U.S. Response to Non-Final Office Action for U.S. Appl. No. 13/010,448, dated Mar. 31, 2014.
Viehland, Christian et al.; "Enhanced volumetric visualization for real time 4D intraoperative ophthalmic swept-source OCT" Biomedical Optics Express 1815, May 1, 2016 | vol. 7, No. 5 |.
Warshall, A Theorem on Boolean Matrices, Computer Associates, Inc., Woburn, Massachusetts, U.S.
Wieser, Wolfgang et al., Multi-Megahertz OCT: High Quality 3D Imaging at 20 Million A-Scans and 4_5 GVoxels Per Second, Optics Express, vol. 18, No. 14, Jun. 30, 2010.
Witte, S., Plaw;;ka, A., Ridder, M. C., van Berge, L., Mansvelder, H. D., & Groot, M. L. (2012). Short-coherence off-axis holographic phase microscopy of live cell dynamics. Biomedical Optics Express, 3(9), 2184-2189. http://doi.org/10.1364/BOE.3.002184.
Yazdanpanah et al., Segmentation of Intra-Retinal Layers from Optical Coherence Tomography Images Using an Active Contour Approach, IEEE, 2010, U.S.
International Preliminary Report on Patentability issued in PCT Application No. PCT/US2016/016900 dated Aug. 8, 2017.
"American National Standard for Safe Use of Lasers" American National Standards Institute, Inc. Mar. 16, 2007.
Aschke et a l., "Augmented Reality in Operating Microscopes for Neurosurgical Interventions." IEEE, Mar. 22, 2003, pp. 652-654 (Mar. 22, 2003), p. 652, col. 2; p. 653, col. 2—p. 653, col. 1; Fig 3 [online].
Goncharov, Alexander V. et al.; "Wide-field schematic eye models with gradient-index lens" J. Opt. Soc. Am. A., vol. 24, No. 8/Aug. 2007, pp. 2157-2174.
Bellman, On a Routing Problem, Richard Bellman, vol. XVI, No. 1, The RAND Corporation, pp. 87-90, 1957, U.S.
Bichlmeier, Christoph et al.; "The Tangible Virtual Mirror: New Visualization Paradigm for Navigated Surgery" Chair for Computer Aided Medical Procedures (CAMP), TU Munich, Germany.
Dabov, Kostadin et al., Image Denoising by Sparse 3-D Transform-Domain Collaborative Filtering, IEEE Transactions on Image Processing, vol. 16, No. 8, Aug. 2007.
Dhalla, Al-Hafeez et al., Complex Conjugate Resolved Heterodyne Swept Source Optical Coherence Tomograph) Using Coherenece Revival, Biomedical Optics Express, vol. 3, No. 3, Feb. 24, 2012.
Dijkstra, A Note on Two Problems in Connexion with Graphs, Cambridge University Press, 1897, vol. 13, p. 26-8, U.K.
International Search Report and Written Opinion dated Aug. 16, 2016 from International Application No. PCT/US16/28862.
International Search Report and Written Opinion dated Aug. 12, 2016 from International Application No. PCT/US16/3105.

Elias, P., et al., A Note on the Maximum Flow Through a Network, IRE Transactions on Information Theory, 1956, pp. 117-119.
Fabritius et al., Automated Segmentation of the Macular by Optical Coherence Tomography, Optics Express, vol. 17, No. 18, Aug. 31, 2009, US.
Farsiu et al., Fast Detection and Segmentation of Drusen in Retinal Optical Coherence Tomography Images, Ophthalmic Technologies XVIII, Proc. of SPIE vol. 6844, 2008, U.S.
Ferguson, R. Deniel et aL, Tracking Optical Coherence Tomography, Optics Letters, vol. 29, No. 18, Sep. 15, 2004.
Fernandez et al., Automated Detection of Retinal Layer Structures on Optical Coherence Tomography Images, Optics Express, vol. 13, No. 25, Dec. 12, 2005, U.S.
Final Rejection received in U.S. Appl. No. 13/353,612 dated May 10, 2017 (eleven (11) pages).
Garvin et al., Automated 3-D Intraretinal Layer Segmentation of Macular Spectral-Domain Optical Coherence Tomography Images, IEEE Transactions on Medical Imaging, vol. 28, No. 9, Sep. 2009, U.S.
Garvin, M.K., et al., Intraretinal Layer Segmentation-Search, IEEE, 0278-0062, pp. 1495-1505, 2008.
Graph cuts segmentation—medical images, Jacquot et al., I EEE,978-0-7695-3122, 2008, pp. 631-635.
Haeker et al., Automated Segmentation of Intraretinal Layers from Macular Optical Coherence Tomography Images, Society of Photo-Optical Instrumentation Engineers, 2007, U.S.
Hendargo, Hansford C. et al., Automated Non-Rigid Registration and Mosaicing for Robust Imaging of Distinct Retinal Capillary Beds Using Speckle Variance Optical Coherence Tomography, Biomedical Optics Express, vol. 4, No. 6, May 7, 2013.
International Search Report and Written Opinion issued in PCT Application No. PCT/US2016/016900 dated May 5, 2016.
International Preliminary Report on Patentability dated Jul. 23, 2013 for corresponding application PCT/US2012/021839 (filed Jan. 19, 2012).
Jung, Woonggyu et al.; "Handheld Optical Coherence Tomography Scanner for Primary Care Diagnostics" IEEE Transactions on Biomedical Engineering, vol. 58, No. 3, Mar. 2011. pp. 741-744.
International Search Report and Written Opinion dated Jan. 5, 2017 from International Application No. PCT/US16/51360.
International Search Report and Written Opinion dated May 19, 2016 from related International Application No. PCT/US16/16830.
Intra-retinal segmentation—images, Mishra et al., Optic Express 23719, Published Dec. 11, 2009, pp. 1-10.
Ishikawa et al., Macular Segmentation with Optical Coherence Tomography, Investigative Ophthalmology & Visual Science, vol. 46, No. 6, Association for Research in Vision and Ophthalmology, Jun. 2005, U.S.
Jaquot, J.Z., et al.,Graph Cuts Segmentation—Medical Images, IEEE, pp. 631-635. 2008.
Ji, Na et al., Adaptive Optics Via Pupil Segmentation for High-Resolution Imaging in Biological Tissues, Nature Methods, vol. 7, No. 2, Feb. 2010.
Kavraki, Lydia E. et al.; "Probabilistic Roadmaps for Path Planning in High-Dimensional Configuration Spaces" IEEE Transactions on Robotics and Automation, vol. 12, No. 4, Aug. 1996.
Koreeda, Y. et al.; "Development and testing of an endoscopic pseudo-viewpoint alternating system" Int J CARS, Jun. 21, 2014.
Kozak, Igor et al.; "Virtual reality simulator for vitreoretinal surgery using integrated OCT data" Clinical Ophthalmology 2014:8 pp. 669-672.
LaRocca et al., "Optimization of confocal scanning laser opthalmoscope design." Journal of Biomedical Optics. Jul. 2013 {Jul. 20, 2013). pp. 076015-1-076015-2, 076015-8 [online].
LaRocca, Francesco et al.; "Handheld simultaneous scanning laser ophthalmoscopy and optical coherence tomography system" Biomedical Optics Express, Nov. 1, 2013 | vol. 4, No. 11, pp. 2307-2321.
LaValle, Steven M. et al.; "Rapidly-Exploring Random Trees: A New Tool for Path Planning" Department of Computer Science, Iowa State University.

(56) References Cited

OTHER PUBLICATIONS

Lee, K., et al. Segmentation of the Optic Disc in 3-D OCT Scans of the Optic Nerve Head. IEEE Transactions on Imaging, vol. 29(1): pp. 159-168, Jan. 2010.

Liao, Wen-Hung et al., Robust Pupil Detection for Gaze-Based User Interface, EGIHMI, Feb. 7, 2010.

Kelly, John P. et al.; "Imaging a Child's Fundus Without Dilation Using a Handheld Confocal Scanning Laser Ophthalmoscope" Arch Ophthalmol/vol. 121, Mar. 2003, pp. 391-396.

Lu et al., Automated Layer Segmentation of Optical Coherence Tomography Images, IEEE Transactions on Biomedical Engineering, vol. 57, No. 10, Oct. 2010, U.S.

Lu, Chen D.; "Handheld ultrahigh speed swept source optical coherence tomography instrument using a MEMS scanning mirror" Biomedical Optics Express, Jan. 1, 2014 | vol. 5, No. 1, pp. 293-311.

Lujan, Brandon J., et al., Revealing Henle's Fiber Layer Using Spectral Domain Optical Coherence Tomography, Investigative Ophthalmology & Visual Science, Mar. 2011, vol. 52, No. 3, 2011.

Martinez-Conde, Susan et al., The Role of Fixational Eye Movements in Visual Perception, Nature Reviews, Neuroscience, vol. 5, pp. 229-240, Mar. 2004.

McNabb, Ryan P_ et al., Distributed Scanning Volumetric SDOCT for Motion Corrected Corneal Biometry, Biomedical Optics Express, vol. 3, No. 9, Aug. 10, 2012.

Scott, Adrienne W. et al.; "Imaging the Infant Retina with a Hand-held Spectral-Domain Optical Coherence Tomography Device" Infant Retina Imaging by Hand-Held SD OCT, vol. 147, No. 2, pp. 364-373.

Mishra, A., et al., Intra-Retinal Segmentatioin-Images, Optic Express 23719, pp. 1-10, Dec. 11, 2009.

Thevenaz, Philippe et al.; "User-Friendly Semiautomated Assembly of Accurate Image Mosaics in Microscopy" Microscopy Research and Technique vol. 70: pp. 135-146 (2007).

Niemeijer et al., Vessel Segmentation in 3D Spectral OCT Scans of the Retina, Medical Imaging 2008, Image Processing, Proc. of SPIE, vol. 6914, 2008, U.S.

Non-Final Office Action received in U.S. Appl. No. 13/010,448 dated Jan. 2, 2014.

Notice of Allowance received in U.S. Appl. No. 13/010,448 dated May 13, 2014.

Aschke et a l., "Augmented Reality in Operating Microscopes for Neurosurgical Interventions." IEEE, Mar. 22, 2003, pp. 652-654 (Mar. 22, 2003), p. 652, col. 2; p. 653, col. 2—p. 653, col. 1; Fig 3 [online] <URL: http://wwwipr.ipr.uni-karlsruhe.de/en/publications/download/id/288/d/article288.pdf>.

International Search Report and Written Opinion (PCT/ISA/220 & PCT/ISA/210 & PCT/ISA/237) issued in PCT Application No. PCT/US2016/016830 dated May 19, 2016 (nine (9) pages).

\* cited by examiner

Left ocular

Right ocular

Left ocular

Right ocular

STEREOSCOPIC DISPLAY SYSTEMS AND METHODS FOR DISPLAYING SURGICAL DATA AND INFORMATION IN A SURGICAL MICROSCOPE

CROSS REFERENCE TO RELATED APPLICATION

This is a 371 national stage patent application, which claims priority to PCT International Patent Application No. PCT/US2016/016830, filed Feb. 5, 2016, and titled STEREOSCOPIC DISPLAY SYSTEMS AND METHODS FOR DISPLAYING SURGICAL DATA AND INFORMATION IN A SURGICAL MICROSCOPE, which claims the benefit of U.S. Provisional Patent Application No. 62/112,698, filed Feb. 6, 2015 and titled STEREOSCOPIC HEADS-UP DISPLAYING SURGICAL DATA IN A SURGICAL MICROSCOPE AND METHODS OF USE, the disclosures of which are incorporated herein by reference in their entireties.

FEDERALLY SPONSORED RESEARCH OR DEVELOPMENT

The technology disclosed herein was made in part with government support under Federal Grant No. EY023039 awarded by the National Institutes of Health (NIH). The United States government has certain rights in the technology.

TECHNICAL FIELD

The present subject matter relates to display systems. More particularly, the present subject matter relates to stereoscopic display systems and methods for displaying medical or surgical data and information in a surgical microscope or other display device designed for interactive use during patient care.

BACKGROUND

First generation intrasurgical optical coherence tomography (OCT) systems displayed OCT data onto a separate computer monitor, requiring surgeons to look away from the surgical microscope. In order to provide real-time OCT feedback without requiring surgeons to look away during surgeries, recent prototype research and commercial intrasurgical OCT systems have integrated heads-up display (HUD) systems into the surgical microscopes to allow the surgeons to access the OCT data and the surgical field through the oculars concurrently. However, current intrasurgical OCT systems with a HUD are only capable of displaying through one ocular or eyepiece, thus limiting the surgeon's depth perception of OCT volumes. Stereoscopy is an effective technology to dramatically increase depth perception by presenting an image from slightly different angles to each eye. Conventional stereoscopic HUD use a pair of micro displays which require bulky optics. Several approaches for HUDs are reported to use only one micro display at the expense of image brightness or increased footprint. However, these techniques for HUD are not suitable to be integrated into microscopes. Other display devices intended for medical, industrial, or entertainment use may also benefit from a more compact and efficient optical design. For example, head-mounted displays, enhanced/augmented reality displays, and other immersive display technologies require compact and light weight designs.

For at least the aforementioned reasons, there is a need for improved display systems for use in medical and other applications.

SUMMARY

Disclosed herein are stereoscopic display systems and methods for displaying surgical data and information in a surgical microscope. In accordance with embodiments of the present disclosure, a compact, microscope-integrated stereoscopic HUD is disclosed which uses spatial multiplexing to project stereo views into both oculars simultaneously using a single micro-display. The HUD is supported by real-time GPU-enabled stereoscopic OCT image processing. In an example, a stereoscopic HUD having one micro display and only three optical elements is provided for a microscope-integrated OCT system.

According to an aspect, a stereoscopic display system includes first and second eyepieces. The system includes a display having first and second display portions, configured to display first images in the first display portion, and configured to display second images in the second display portion. The first image and the second image are projected along a first pathway and a second pathway leading to the first and second eyepiece, respectively. The system includes a first beamsplitter or other optical element positioned so that the first eyepiece only receives the first images, and positioned to receive and reflect both first and second light into the first microscope optical path but the received second light is rejected by the aperture inside the first eyepiece or any suitable aperture. The system includes a second beamsplitter or other optical element positioned so that the second eyepiece only receives the second images, and positioned to receive and reflect both first and second light into the second microscope optical path but the received first light is rejected by the aperture inside the second eyepiece or any suitable aperture.

BRIEF DESCRIPTION OF THE DRAWINGS

The foregoing aspects and other features of the present subject matter are explained in the following description, taken in connection with the accompanying drawings, wherein.

DETAILED DESCRIPTION

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "about" is understood as within a range of normal tolerance in the art, for example within 2 standard deviations of the mean. The term "about" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

Unless otherwise defined, all technical terms used herein have the same meaning as commonly understood by one of ordinary skill in the art to which this disclosure belongs.

In accordance with embodiments of the present disclosure, a compact, stereoscopic display system is provided for displaying stereoscopic images utilizing a single micro display for Microscope Integrated OCT (MIOCT). In an example, a MIOCT sample arm may couple the OCT and surgical optical axis and may enable concurrent imaging with both systems. Further, it has been demonstrated that high speed Swept-Source MIOCT (SS-MIOCT) may be used for real-time volumetric imaging of dynamic surgical maneuvers.

Figure 1:
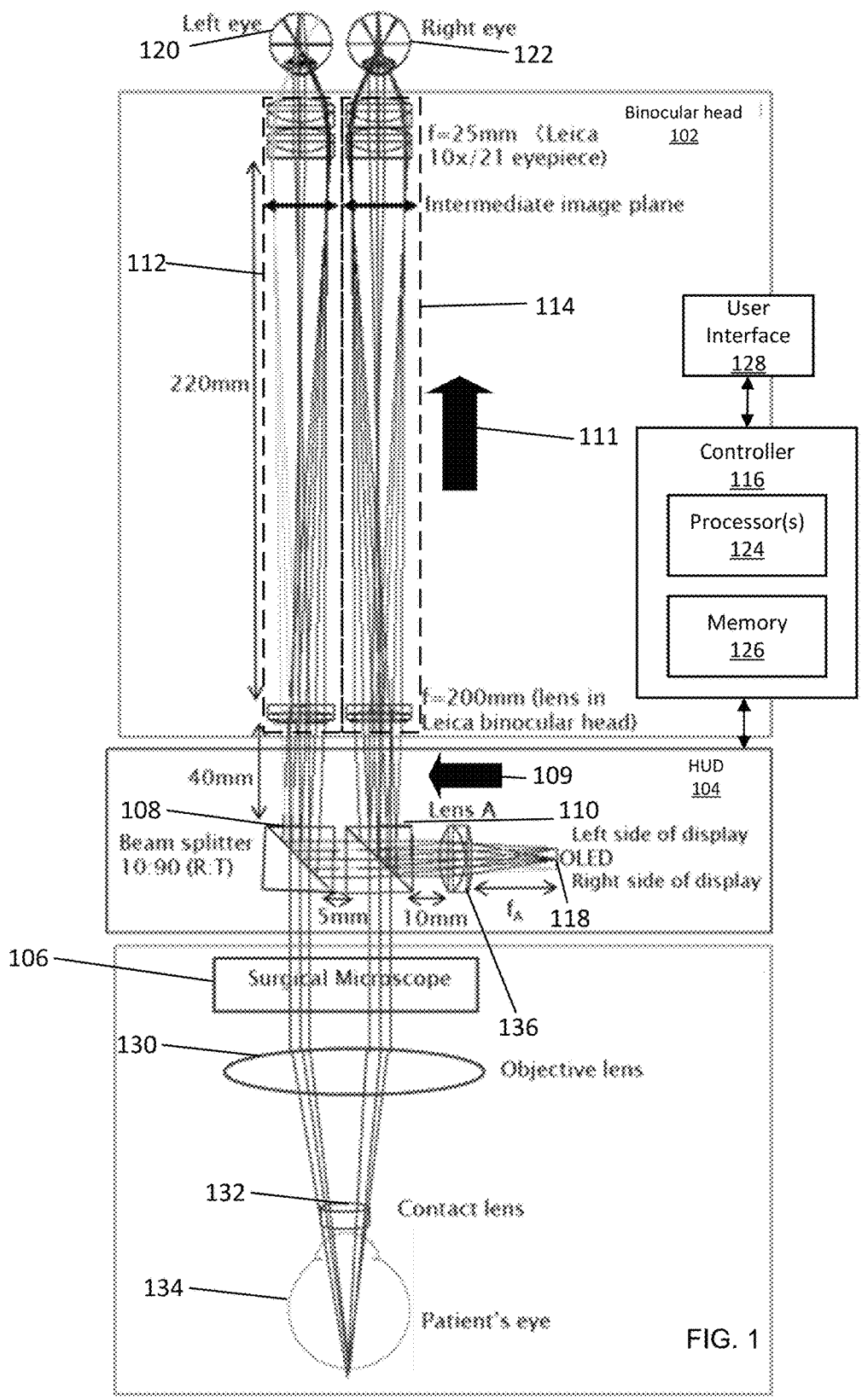
FIG. 1 is a schematic diagram of an example stereoscopic display system in accordance with embodiments of the present disclosure.

FIG. 1 illustrates a schematic diagram of an example stereoscopic display system 100 in accordance with embodiments of the present disclosure. Referring to FIG. 1, system 100 may generally includes a binocular head 102, a stereoscopic HUD 104, and a surgical microscope 106. The HUD 104 may be mounted on the surgical microscope 106. In an example, the surgical microscope 106 may be a ophthalmic surgical microscope (e.g., an M840 microscope available from Leica Microsystems Inc., of Buffalo Grove, Ill.). The HUD 104 includes two beam splitters 108 and 110 positioned to optically couple with both eyepieces (or oculars) 112 and 114, respectively. During operation of the system 100, a controller 116 may control an OLED micro display 118 to display images and/or video. As will be described in more detail herein, the display 118 may include two display portions (e.g., left side and right side of display) that are controlled by the controller 116 to display different images (or video) in the display portions. The different images are projected along two different pathways (generally in the direction indicated by arrow 109) towards the beam splitters 108 and 110. Beam splitter 108 and 110 are positioned to receive both images along both pathways. The beam splitters 108 and 110 are positioned to relay their received images along two pathways (generally in the direction indicated by arrow 111) onto an aperture inside eyepieces 112 and 114 or any suitable aperture, respectively. The aperture inside eyepiece 112 or any suitable aperture only passes a respective pathway from one of the display portions, and the aperture inside eyepiece 114 or any suitable aperture only passes a respective pathway from the other display portion. In this way, the left eye 120 and the right eye 122 of a person can view the projected images of the different display portions of the display 118 in different eyes. The images projected by the display portions of the display 118 are the two different parts of a stereoscopic view. As will be described in more detail herein, such a stereoscopic view can be, for example, overlaid on one or more objects being viewed with the surgical microscope 106 or presented in conjunction with object(s) being viewed with the surgical microscope 106.

The controller 116 can include one or more processors 124 and memory 126 for implementing the function of controlling the display 118 in accordance with embodiments disclosed herein. In an example, the controller 116 may be part of a computing device, such as a desktop computer, a laptop computer, a tablet computer, smartphone, or the like configured with equipment for interfacing with the display 118. The controller 116 may be operably connected to a user interface such that a user may input commands and be presented with data about operation of the system 100, including operation of the display 118. Alternative to the processor(s) 124 and the memory 126, the controller 116 may include any suitable hardware, software, firmware, or combinations thereof for implementing the functionality described herein.

The surgical microscope 106 may be any suitable type of microscope. In this example, the surgical microscope 106 is configured to operate together with an objective lens 130 and contract lens 132 for viewing of a patient's eye 134 during surgery.

In the example of FIG. 1, the display 118 is an OLED micro display (SVGA050, resolution: 800×600, viewing area: 10.13 mm×7.61 mm, pixel pitch: 12.6 μm, contrast ratio: 10,000:1; Yunnan OLiGHTEK Opto-Electronic Technology Co., Ltd.; China). The images displayed by the display 118 can be relayed to the surgeon's eyes by a triplet focusing lens 136 ($f_A$=90 mm; Leica Microsystems Inc.; Buffalo Grove, Ill.) and the microscope eyepiece 112 and 114. Beams splitters 108 and 110 (e.g., beamsplitters available from Thorlabs, Inc.; Newton, N.J.) coupled the HUD 104 and surgical microscope 106 optical axis: 10% of the light from the display 118 can be reflected by beam splitter 110, directing the light into the right eyepiece 114. The remaining light transmitted by the first beam splitter 110 was reflected (10%) by a second splitter 108, directing the light into the eyepiece 112. The beam splitters 108 and 110 were tilted by 1.5±0.25 degree relative to the rest of the optical elements. The angles of both tilted beam splitters 108 and 110 are calibrated so that the left ½ of the display was directed to the right eyepiece 114 while the right ½ of the display was directed to the left eyepiece 112. Tilting of the beam splitter results in a slight lateral displacement of collimated light from the infinity space of the surgical field due to refraction at the glass/air interfaces, but with no displacement of the image position on the observer's retina. The lateral shift due to a 1.5 degree tilt was calculated to be 0.23 mm, which causes negligible vignetting at the ocular stops.

The HUD 104 may be interfaced with an SS-MIOCT system via USB, HDMI, or the like. The HUD 104 can enable real-time acquisition, processing, and stereoscopic HUD display of volumetric images in real time (up to 10 volumes/sec). GPU-based software may be run by the controller 116 to implement functionality disclosed herein. For example, the controller 116 can enable simultaneous rendering of two separate views of each volume which can be displayed in the separate display portions of the display 116. The two renderings can be rotated relative to each other to create the stereoscopic effect. The volume projected to the left eye can displayed in the right ½ of the display 118 which can only be seen by the left eye. The OCT volume intended for the right eye can be rotated 10° (or any other suitable angle) from that intended for the left eye and displayed in the left ½ of the display 118 which can only be seen by the right eye. The positions of the two images can be calibrated experimentally so that they may be fused by the observer. Furthermore, the overall direction of view of both stereoscopic OCT volumes may be rotatable by a control device (e.g., a foot trackball available from Infogrip, Inc.; Ventura, Calif. or other common computer input device) by the surgeon or other user while operating in real time.

Figures 9A, 9B, 9C, 9D:
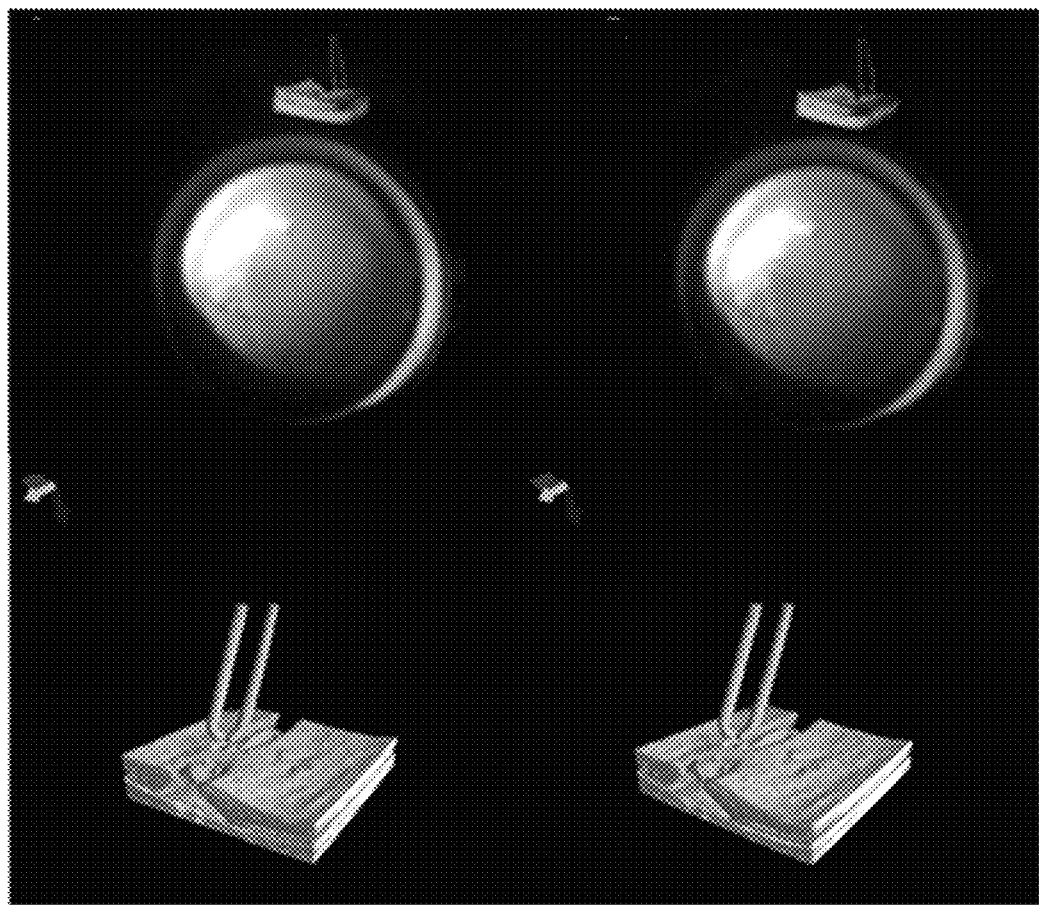
FIGS. 9A and 9B are images seen through the left/right eyepieces in porcine eye operation.
FIGS. 9C and 9D are closeups of stereo pair of volumetric renderings (rotated 9 degrees relative to each other), projected into left/right eyepieces during live human macular surgery.

In experiments, the resolution of the microscope with and without the HUD were measured by imaging USAF 1951 resolution bars. Fields of view were measured by imaging a grid paper. The measured resolution and field of view of the surgical field with and without the HUD were both 12.40 µm and 270 mm² indicating that the HUD did not affect the original field of view of the surgical microscope. Stereoscopic volumetric renders of simulated retinal surgery were acquired by SS-MIOCT and displayed via the HUD. The images used to create the stereoscopic effect inside the HUD oculars are shown in FIGS. 9A and 9B, which are example images seen through both eyepieces of the HUD 104. More particularly, FIG. 9A is the image seen through the left eyepiece, and FIG. 9B is the image seen through the right eyepiece. The round object shown in the images of FIGS. 9A and 9B is the working area of the surgical field of the retina through a contact lens. The brightness of the left eyepiece image was not noticeably different from that of the right eyepiece. The stereoscopic effect of the volume was prominent when observers looked into both eyepieces. Importantly for an overlay display, the use of an OLED display can allow for black pixels to be completely transparent.

In accordance with embodiments of the present disclosure, any suitable type of display may be used. For example, a micro display (SXGA060, resolution: 1280×1024, viewing area: 11.941×9.560 mm, pixel pitch: 9.3 µm and contrast ratio: >10000:1, Yunnan OLiGHTEK Opto-Electronic Technology Co., Ltd.; China) may be used.

An objective lens 136 may be used to focus the display 118. The lens may be any suitable type of lens, such as a triplet lens. The triple lens 136 may have a focal length of 50 mm so that the image is magnified enough to show half of the screen to each eye. Distortion and stereoscopic effect may also be characterized carefully. The rotation angle between two volumes intended to different eyes can be suitably optimized.

Figure 2A:
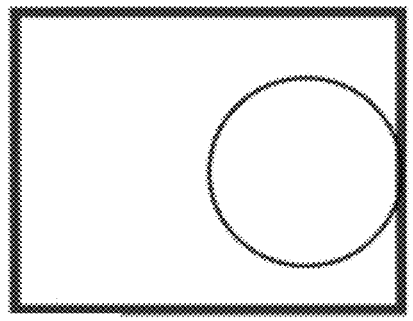
FIGS. 2A-2F illustrate diagrams depicting example images that can be seen through a stereoscopic display system in accordance with embodiments of the present disclosure.
Figure 2B:
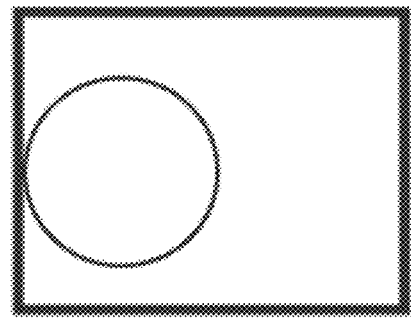
Figure 2C:
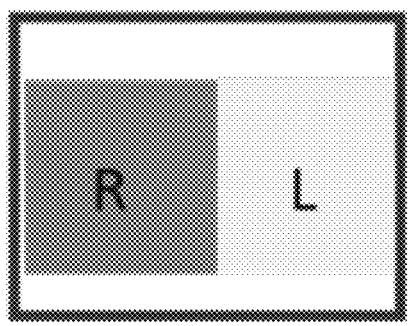
Figure 2D:
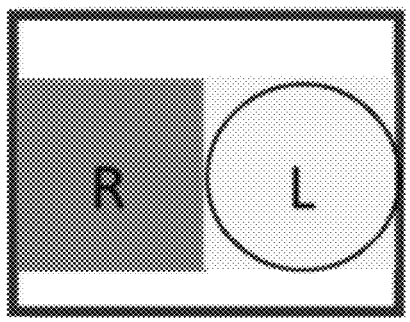
Figure 2E:
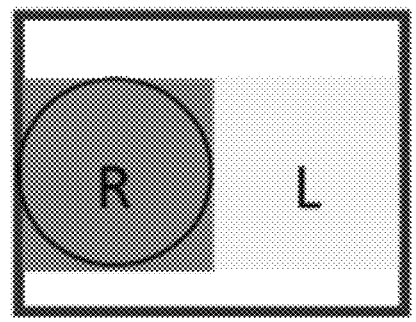
Figure 2F:
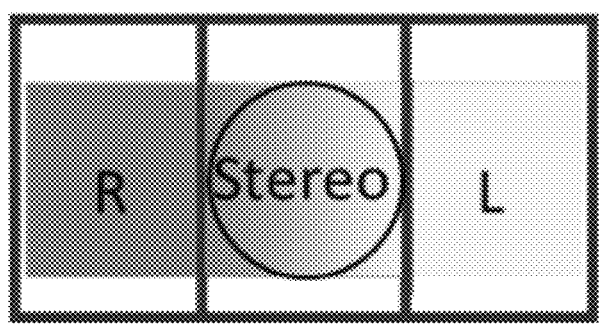

FIGS. 2A-2F illustrate diagrams depicting example images that can be seen through a stereoscopic display system in accordance with embodiments of the present disclosure. For example, the images are examples that may be seen through the system 100 of FIG. 1. Referring to FIGS. 2A and 2B, the figures show images that may be seen through two different eyepieces of the system. The black circles represent the field of view of the eyepieces and the squares represent the position of the display image on the two eyepieces. FIG. 2C shows an image displayed on the display with the two different display portions R (corresponding to the right eyepiece) and L (corresponding to the left eyepiece). FIGS. 2D and 2E show images seen through the respective eyepieces (right and left) when the HUD projects corresponding images intended for the different eyes. FIG. 2F shows stereoscopic images fused by the observer's brain.

Figure 3:
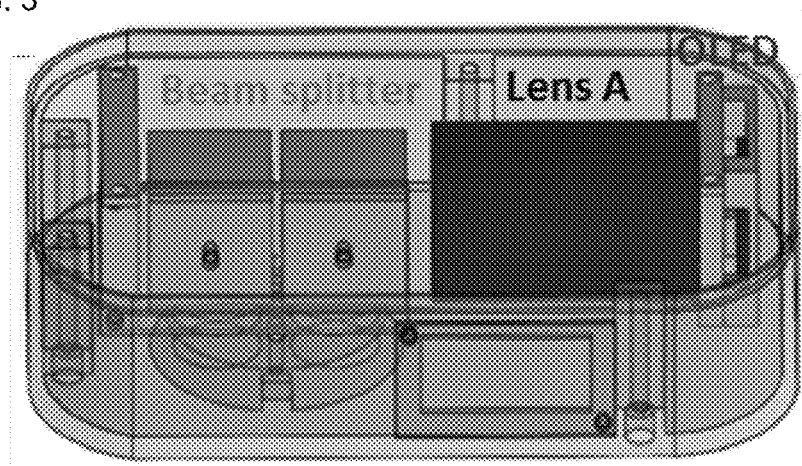
FIG. 3 is a partially transparent view of a HUD in accordance with embodiments of the present disclosure.
Figure 4:
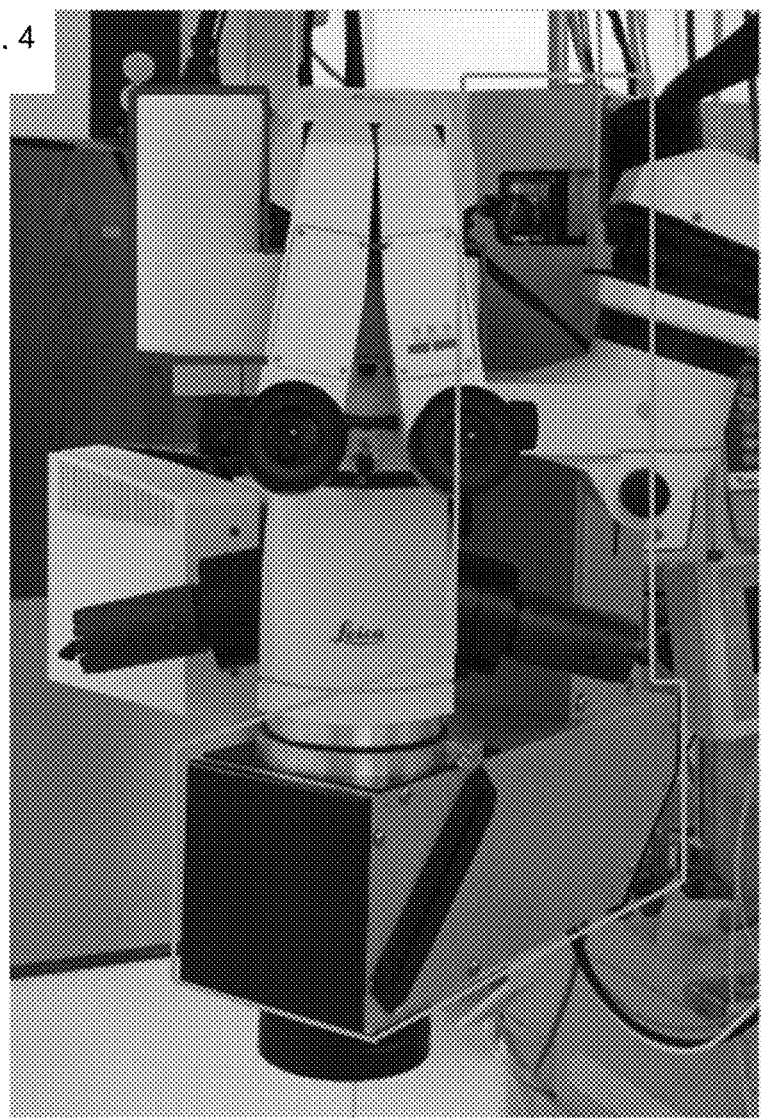
FIG. 4 is an image of a HUD mounted on a surgical microscope attached with an SSOCT scan head in accordance with embodiments of the present disclosure.

In accordance with embodiments of the present disclosure, a camera connected with a camera lens may be attached to a surgical microscope's eyepiece with a 3D printed mount for capturing images on the microscope's surgical plane and the HUD's display plane. The camera may be any suitable camera, such as a camera provided by Point Grey Research, http://www.ptgrey.com. The camera lens (e.g., 8.5 mm) may be any suitable lens, such as a lens provided by Edmund Optics Inc., of Barrington, N.J. As a further example, FIG. 3 illustrates a partially transparent view of a HUD in accordance with embodiments of the present disclosure. FIG. 4 is an image of a HUD mounted on a surgical microscope attached with an SSOCT scan head in accordance with embodiments of the present disclosure.

Figure 6:
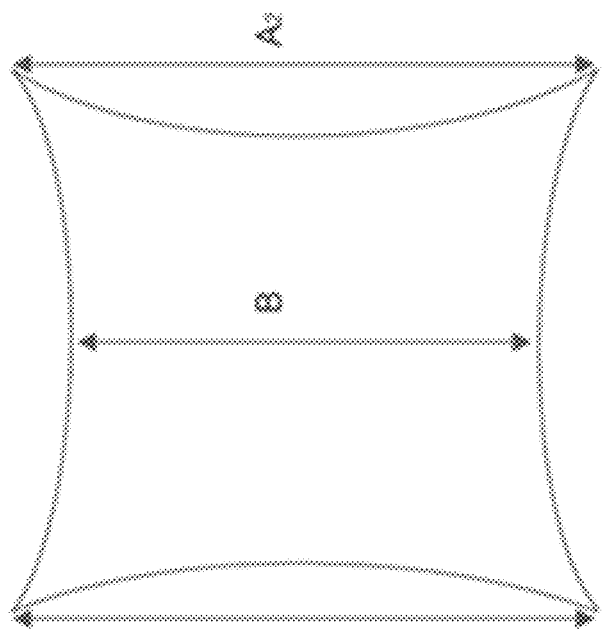
FIG. 6 illustrates a diagram of pincushion distortion.
Figure 5:
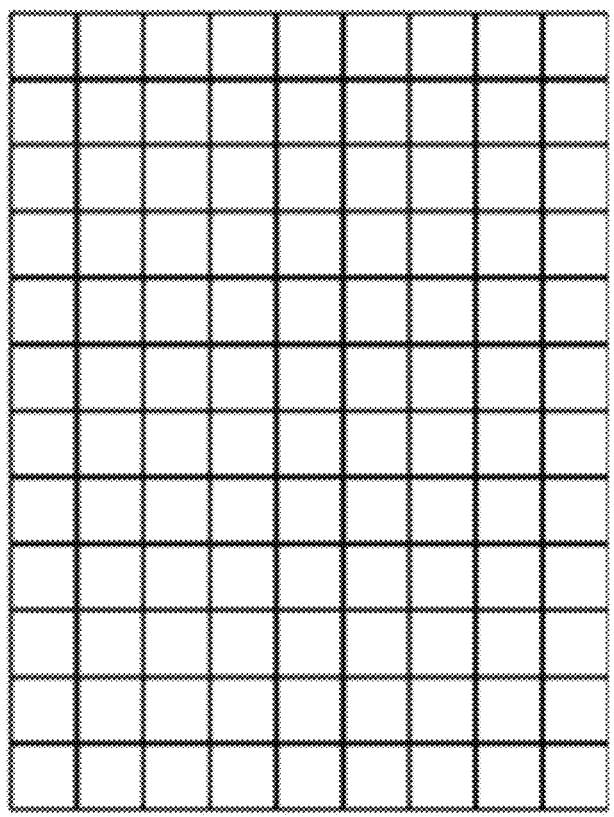
FIG. 5 depicts a grid test chart for distortion characterization.

In order to characterize the effects of the addition of the HUD on the optical path of the operating microscope, resolution, field of view (FOV), and distortion of the surgical microscope with and without the HUD was measured with a USAF resolution test target, a caliper, and a grid chart respectively in the surgical field at 10× total magnification. FIG. 5 depicts a grid test chart for distortion characterization. FIG. 6 illustrates a diagram of pincushion distortion. The distortion of the HUD's display and captured by a camera through the microscope eyepieces. The captured grid chart images were then analyzed by Imatest software (available from Imatest LCC of Boulder, Colo.) in which SMIA TV distortion was calculated by this software based on the following equation (1) and FIGS. 3A-3F.

$$SMIA \text{ TV Distortion } (\%) = \frac{100(A - B)}{B}, A = \frac{A_1 + A_2}{2} \quad (1)$$

Figure 7:
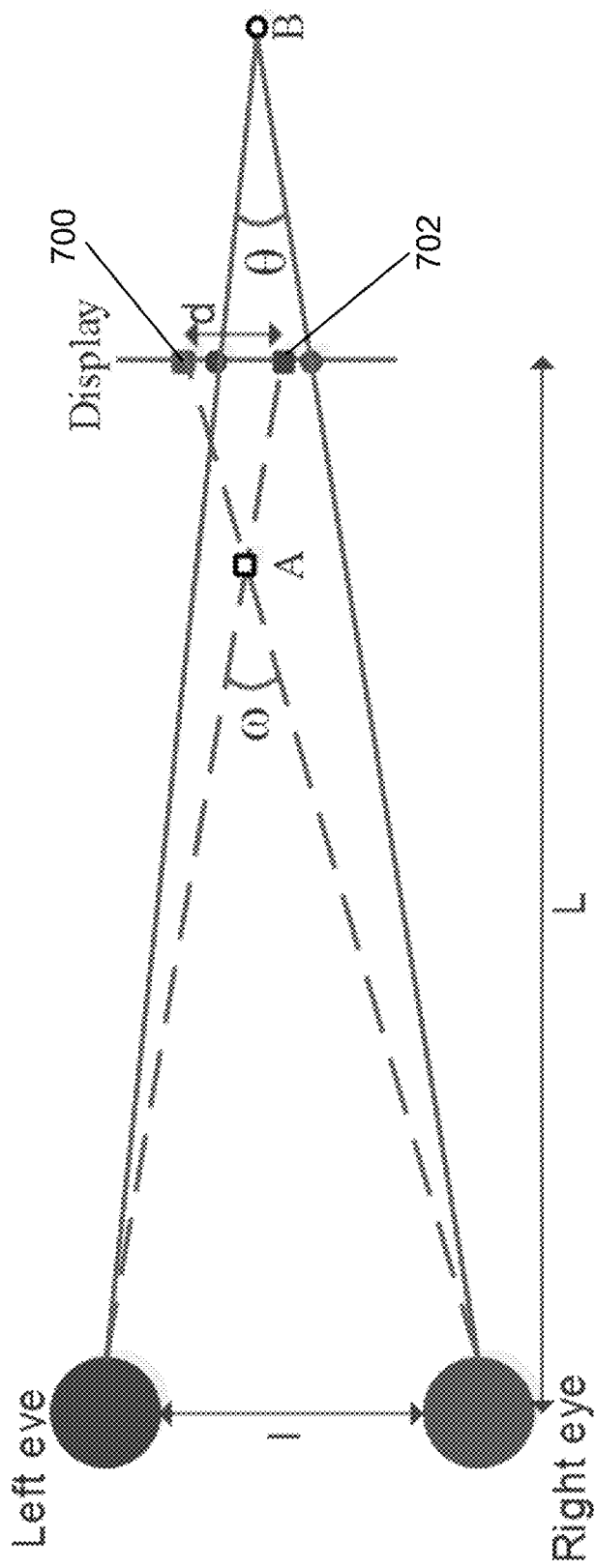
FIG. 7 is a diagram depicting a stereopsis example.

Stereopsis is one of the strongest depth cues where human brains reconstruct distance according to lateral displacement between two points perceived by left and right eyes. As two objects like square 700 and square 702 in FIG. 7 are displayed in a 3D viewing device in which one object is only projected to one eye, both eyes can be fixated at a point of interest like point A through vergence. The disparity for point B when eyes are fixated at point A is measured by angular parallax (ω−θ). If the angular parallax exceeds an upper limit, double vision (diplopia) will be experienced. In an experimental study, the upper limit of angular parallax varies dramatically from people to people and found to be around 4-7°. In this example application, the virtual image of the rendered OCT volume relayed by the microscope eyepiece had a size of 50 mm wide and 50 mm height, 250 mm (L) away from the observers. The maximum lateral displacement (d) between two same points intended to different eyes was set to be 6 mm. The Interpupillary distance of the observer was assumed to be 65 mm (I). Thus, the angular disparity (ω−θ) can be calculated by equation (2).

$$\omega - \theta = 2x\arctan\left(\frac{l+d}{2L}\right) - 2x\arctan\left(\frac{l-d}{2L}\right) \quad (2)$$

Some objects on the display can only be seen by the left eye while other objects can only be seen by the right eye. Through vergence, both eyes can be fixated at point A or point B which appear to be above or beneath the display.

Figures 8A, 8B, 8C:
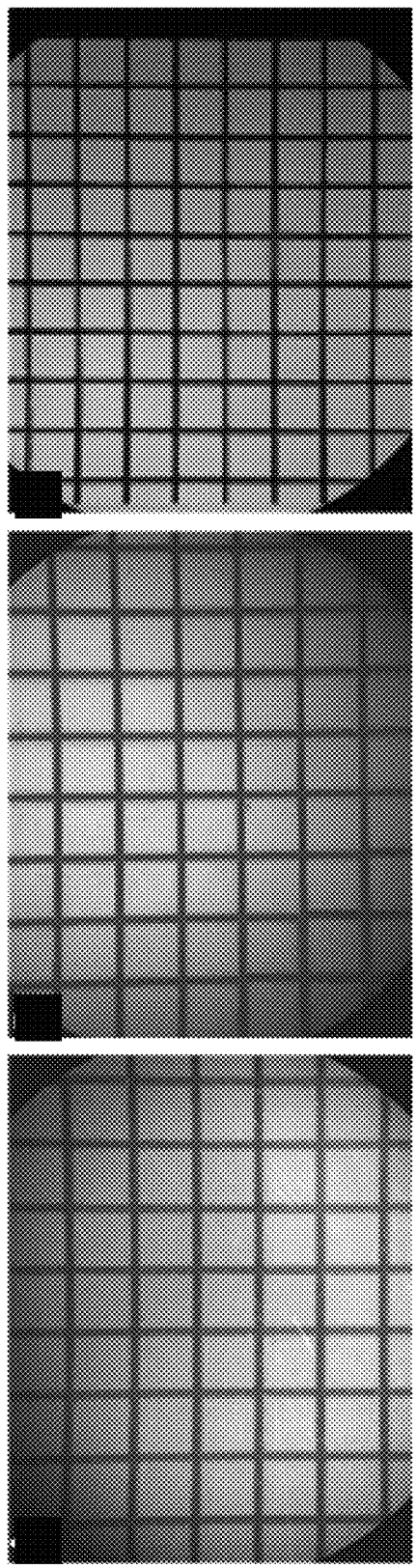
FIGS. 8A-8C are images captured through eyepieces in accordance with embodiments of the present disclosure.

The grid charts placed in the surgical field of the microscope with or without the HUD mounted were imaged through microscope oculars (see FIGS. 9A and 9B). It can be seen that both images have small and same degrees of pincushion distortions. The quantitatively characterized resolution, FOV and SMIA TV distortion of Leica M844 surgical microscope with and without HUD are reported in Table 1. From the data and image, it is clear that the addition of HUD in the optical path of the microscope had little to no effects to the optical performance of the microscope. FIGS. 8A-8C are images captured through eyepieces in accordance with embodiments of the present disclosure. Particularly, FIG. 8A is an image captured when a grid chart was placed in the microscope surgical field without HUD mounted. FIG. 8B is an image captured when the grid chart was placed in the microscope surgical field with HUD mounted. FIG. 8C is an image captured when the grid chart image was displayed the HUD's display.

The distortion of the HUD's optical system was also characterized by the same grid chart pattern (see FIG. 8C) and was found to be 1.21%, which indicates that the optical system of the HUD had decent optical performance to display intra surgical data. The maximum angular parallax in the rendered OCT volume was calculated to be 2.7°. Most observers should be able to fuse the stereoscopic volume easily when looking through the HUD systems.

Table 1 below shows a comparison of resolution, FOV, and distortion between microscope with HUD and without HUD.

TABLE 1

| Characteristics | Microscope without HUD | Microscope with HUD |
| --- | --- | --- |
| Resolution (μm) | 12.40 | 12.40 |
| FOV (mm) | 21 | 21 |
| SMIA TV Distortion (%) | 1.47 (pincushion) | 1.56 (pincushion) |

Stereoscopic, 4D Microscope Integrated OCT (4DMIOCT) volumetric renders of human retinal surgery have been acquired and displayed via the HUD (see FIGS. 9A-9D). FIGS. 9A and 9B are example images that can be viewed through eyepieces of a HUD in accordance with embodiments of the present disclosure. FIG. 9A shows an image viewable through a left eyepiece. FIG. 9B shows an image viewable through the right eyepiece. The round object in the figures is the surgical view of the retina through a contact lens. FIGS. 9C and 9D are closeups of stereo pair of volumetric renderings (rotated 9 degrees relative to each other), projected into left/right eyepieces during live human macular surgery. The brightness of the left ocular image was not noticeably different from that of the right ocular. Up to the time when the application is submitted, 43 human vitreoretinal surgeries have been operated with the HUD. A total number of five ophthalmic surgeons have used the HUD during simulated surgeries or human vitreoretinal surgeries and all of them reported able to see prominent stereoscopic effect when they looked into both oculars. For an overlay display, the use of an OLED display can allow completely transparent black pixels (contrast=10000:1), unlike liquid crystal on silicon (LCOS) micro displays used in prior work, to ensure that operating microscope view through the HUD was not compromised.

Figure 10:
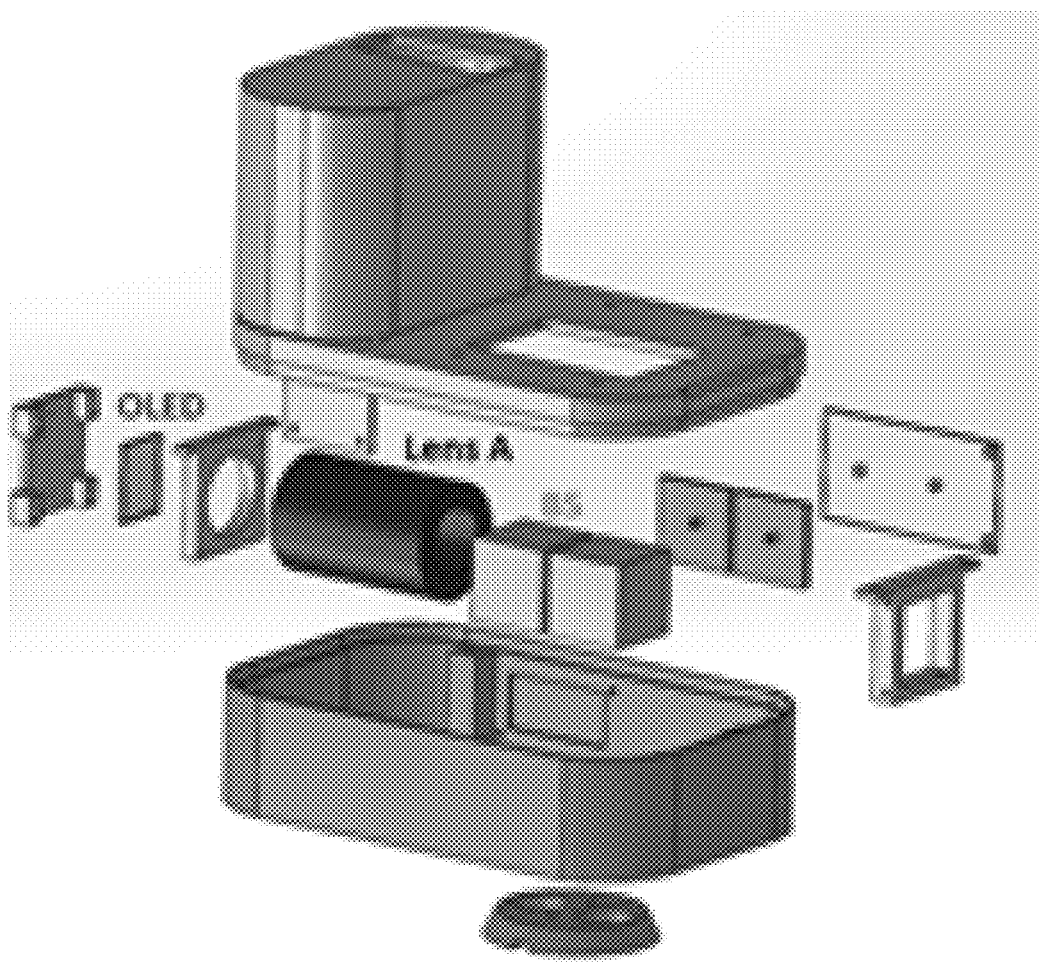
FIG. 10 is an exploded perspective view of a HUD in accordance with embodiments of the present disclosure.
Figure 11:
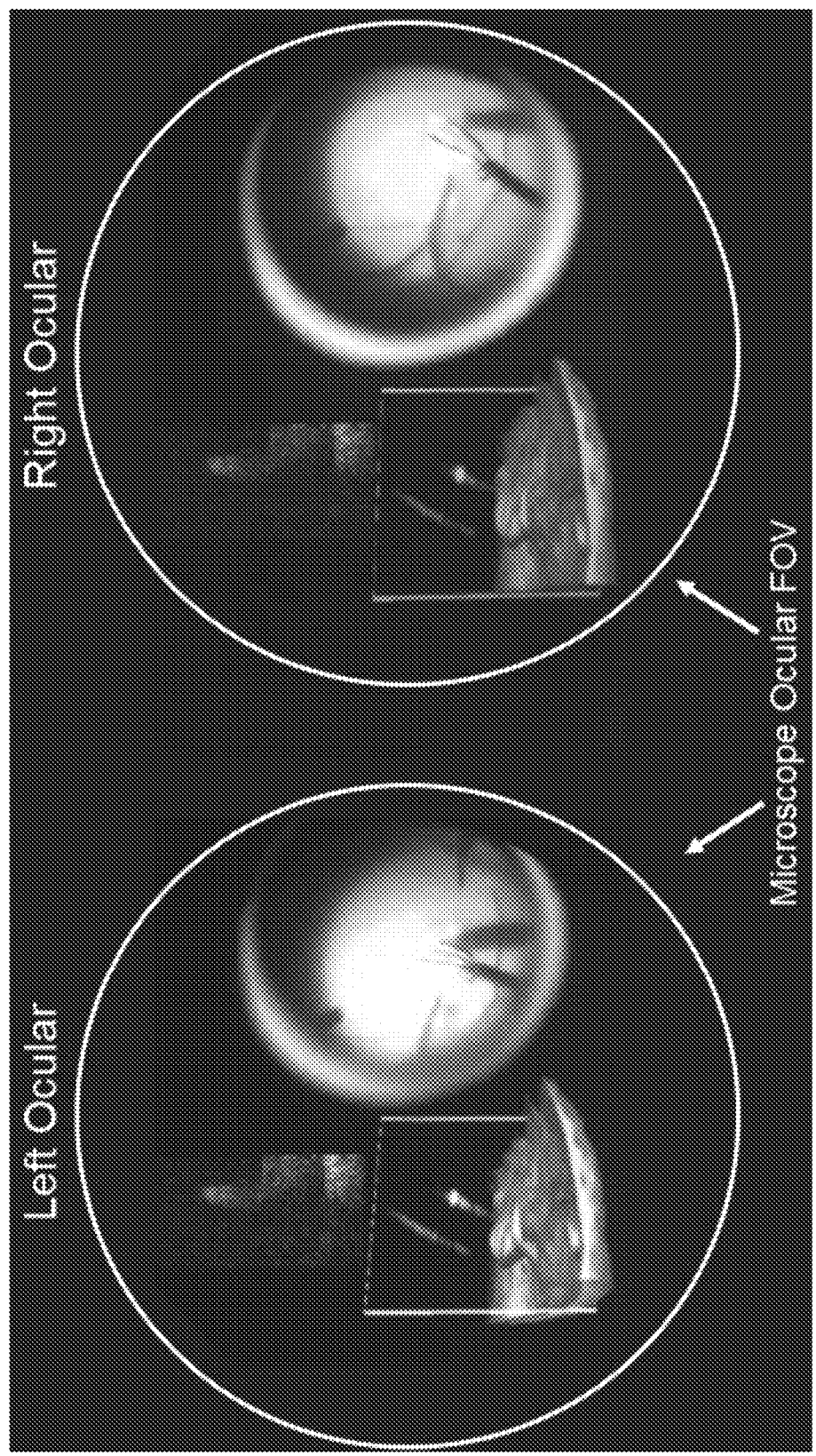
FIG. 11 illustrates two different field of views shown in oculars (or eyepieces) in accordance with embodiments of the present disclosure.
Figure 12:
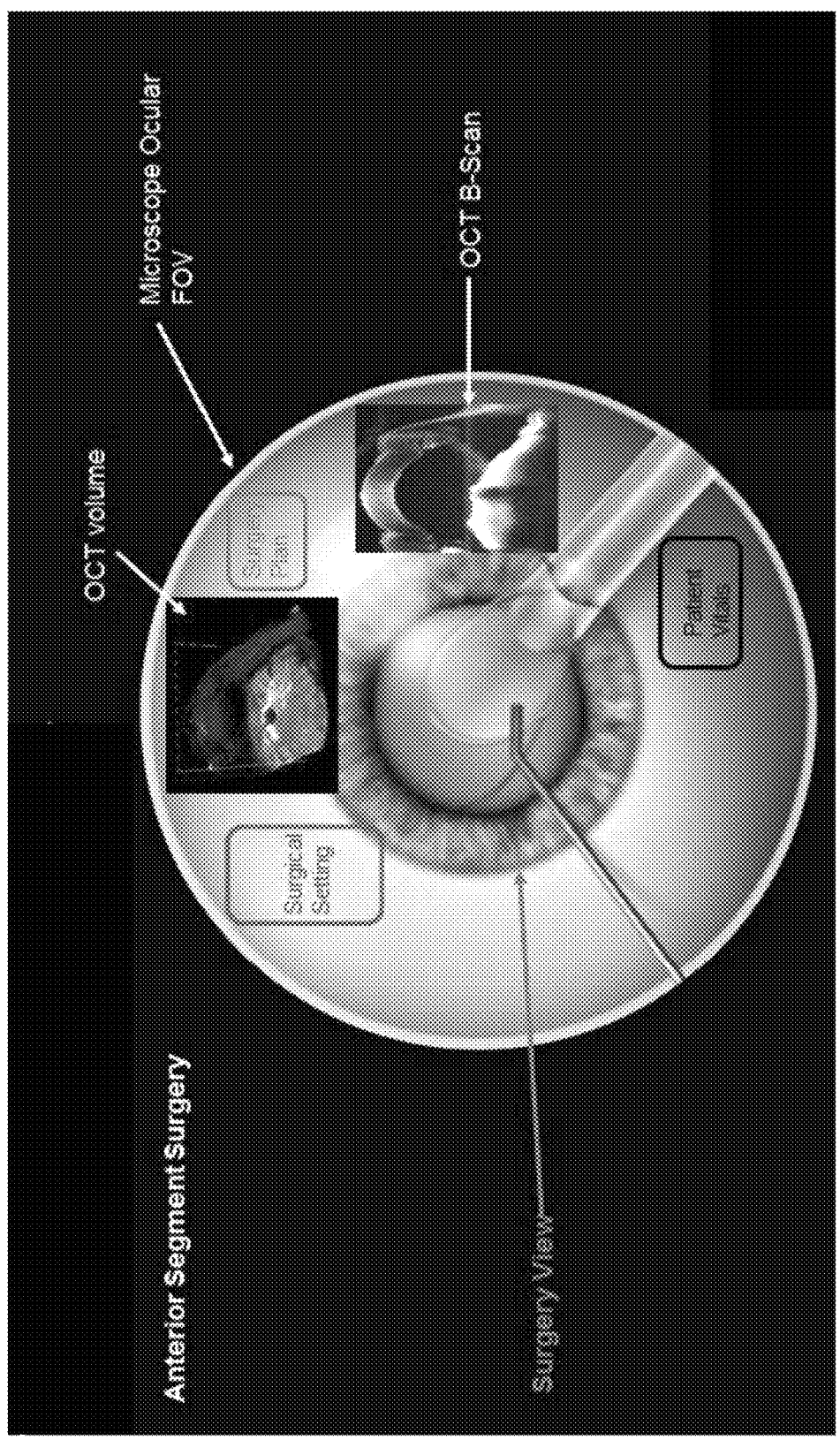
FIG. 12 illustrates an image showing an example HUD image in accordance with embodiments of the present disclosure.

FIG. 10 illustrates an exploded perspective view of a HUD in accordance with embodiments of the present disclosure. Referring to FIG. 11, the HUD includes an OLED, lens, and beam splitters as shown.

FIG. 11 illustrates two different field of views shown in left and right oculars (or eyepieces) in accordance with embodiments of the present disclosure. FIG. 11 also represents a possible display format of MIOCT B scans, volumes and microscope view during wet-lab based studies and live human ophthalmic surgeries. Referring to FIG. 11, OCT images may be displayed on unused peripheral regions inside the oculars which may allow the surgeon an unobstructed view of the working area of the surgical field and of the real time stereoscopic OCT data simultaneously. The surgeon may use a foot-controlled device or any other suitable devices to interact with displayed images (e.g. orienting OCT volumes to inspect an interested area from different angles). According to the surgeons, the HUD was intuitive to use, did not restrict or alter their normal view of surgery, and that the stereoscopic OCT volumes rendered in the HUD were readily visible. Additionally, all reported that the small brightness difference between left and right ocular images was not discernable and surgeons preferred stereoscopic to monoscopic visualization of MIOCT volumes for improved depth perception.

Figure 13:
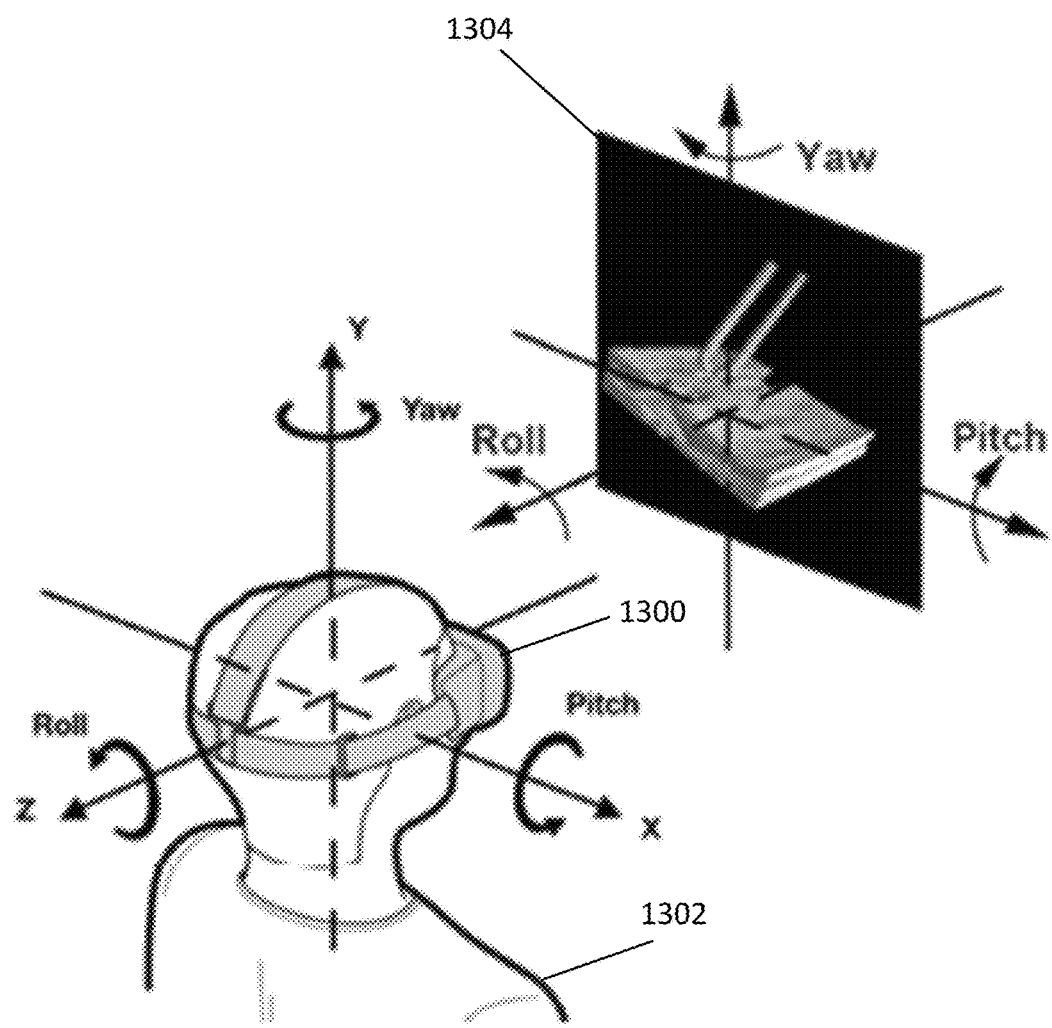
FIG. 13 is a perspective view of example movement tracking equipment 1400 in use in accordance with embodiments of the present disclosure.

FIG. 13 illustrates an image showing an example HUD image in accordance with embodiments of the present disclosure. Referring to FIG. 13, the HUD can include the surgery view as well as other images projected by a display. The other images may include surgical setting information, surgery plan information, and patient vital information. Further, the display can project images of an OCT volume and an OCT B-scan.

In accordance with embodiments of the present disclosure, a compact stereoscopic display system may also be incorporated into a head-mounted display unit or any suitable 3D viewing devices intended for medical, industrial, or entertainment use. Whether used with a microscope-integraded HUD, head-mounted display, or any suitable 3D viewing devices, the display system may also include user head movement tracking equipment configured to track movement of a user. The system may include a controller operably connected to the display and configured to alter images displayed by one display portion and another display portion based on the tracked movement. For example, FIG. 14 illustrates a perspective view of a head-mounted stereoscopic display 1400 which also incorporates head tracking equipment (either in the head-mounted display unit itself or configured separately) in use in accordance with embodiments of the present disclosure. Referring to FIG. 14, the head-mounted display 1400 used in conjunction with head movement tracking equipment allows the user to visualize a three dimensional image 1404 from a viewpoint which is intuitively controlled by the user by rotation or transtlation of the user's head. As illustrated in FIG. 14, the head tracking equipment may monitor the roll, pitch and yaw of the user's head in order to control the roll, pitch and yaw of the 3D dataset displayed. Alternatively, the translation of the user's head in x, y, and z may also be monitored in order to intuitively control the user's viewpoint of the 3D dataset. The head tracking equipment and method of use described in this paragraph may also be used together with the microscope-integrated HUD described previously for the user to intuitively control the viewpoint of the rendered dataset.

With continuing reference to FIG. 14, an image 1404 can be captured of a surgical field. A controller, such as controller 116, is configured to alter views shown in the images based on the movement tracked by the head tracking equipment. In this example, the movement of the head can result in corresponding movement about an object shown in the image 1404. In this way, the user 1402 can manipulate the view in the image 1404 without the user of hands.

The various techniques described herein may be implemented with hardware or software or, where appropriate, with a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the presently disclosed subject matter. In the case of program code execution on programmable computers, the computer will generally include a processor, a storage medium readable by the processor (including volatile and non-volatile memory and/or storage elements), at least one input device and at least one output device. One or more programs may be implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims. One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed:

1. A stereoscopic display system comprising:
a display comprising first and second display portions, with an optical system configured to display one or more first images in a first eye interface, and configured to display one or more second images in a second eye interface, and wherein the one or more first images and the one or more second images are projected along a first pathway and a second pathway, respectively;
a first optical element positioned to receive both images projected along both pathways, configured to only allow the one or more first images to pass into the first eye interface; and
a second optical element positioned to receive both images projected along both pathways, configured to only allow the one or more second images to pass into the second eye interface.

2. The stereoscopic display system of claim 1, wherein the one or more first and second images are transmitted through the first optical element before being reflected by the second optical element.

3. The stereoscopic display system of claim 2, wherein the first and second optical elements are tilted with respect to each other so as to direct the one or more first images and one or more second images into the first and second eye interfaces, respectively.

4. The stereoscopic display system of claim 3, wherein the one or more first images are blocked from the second eye interface by a first optical aperture, and wherein the one or more second images are blocked from the first eye interface by a second optical aperture.

5. The stereoscopic display system of claim 4, wherein the first optical aperture is the aperture of the second eye interface or any suitable aperture, and wherein the second eye interface is the aperture of the first eye interface or any suitable aperture.

6. The stereoscopic display system of claim 1, wherein the display is an organic light-emitting diode (OLED) micro display, a digital light processing (DLP) micro display, a liquid crystal micro display (LCD), liquid crystal on silicon (LCOS) micro display or any suitable type of display.

7. The stereoscopic display system of claim 1, wherein the one or more first images and/or the one or more second images comprise optical coherence tomography (OCT) images or any suitable images.

8. The stereoscopic display system of claim 1, further comprising a microscope operably connected to the first and second display portions, and configured to transfer first and second images of a sample to the display portions.

9. The stereoscopic display system of claim 8, wherein the movement tracking equipment comprises a head tracker configured to track movement of the head of the user.

10. The stereoscopic display system of claim 8, wherein the images comprise images of a surgical field, and
wherein the controller is configured to alter views shown in the images based on the tracked movement.

11. The stereoscopic display system of claim 1, further comprising an objective lens operably positioned along the first and second pathways between the display and the first and second beamsplitters.

12. The stereoscopic display system of claim 11, wherein the objective lens is a triplet lens or any suitable lens.

13. The stereoscopic display system of claim 1, wherein the first optical element and the second optical element are angled relative to each other and the rest of the optical elements.

14. The stereoscopic display system of claim 13, wherein the angle is 3±0.5 degrees or any suitable angle relative to each other and 1.5±0.25 degrees or any suitable angle relative to other optical elements.

15. The stereoscopic display system of claim 1, wherein the two optical elements are positioned in microscope's left and right optical path, respectively and are on the same horizontal plane with the micro display and focusing lens.

16. The stereoscopic display system of claim 1, further comprising:
movement tracking equipment configured to track movement of a user; and
a controller operably connected to the display and configured to alter images displayed by the first display portion and the second display portion based on the tracked movement.

17. The stereoscopic display system of claim 1, wherein the stereoscopic display system may also be incorporated into a head-mounted display unit or any suitable viewing devices intended for medical, industrial, or entertainment use.

* * * * *